United States Patent
Arnold

[19]
[11] Patent Number: 6,155,097
[45] Date of Patent: Dec. 5, 2000

[54] METHOD AND APPARATUS FOR SELECTIVELY EXTRACTING AND COMPRESSING TRACE SAMPLES FROM A CARRIER TO ENHANCE DETECTION

[75] Inventor: James T. Arnold, Cupertino, Calif.

[73] Assignee: Varian, Inc., Palo Alto, Calif.

[21] Appl. No.: 09/087,666

[22] Filed: May 29, 1998

[51] Int. Cl.[7] .......................... G01N 30/04; G01N 30/08
[52] U.S. Cl. ...................... 73/23.35; 73/23.42; 422/89; 422/101
[58] Field of Search ................. 73/23.35, 23.4, 73/23.42; 422/83, 89, 101

[56] References Cited

U.S. PATENT DOCUMENTS

| | | |
|---|---|---|
| 3,427,863 | 2/1969 | Schultz . |
| 3,471,692 | 10/1969 | Llewellyn et al. . |
| 3,772,909 | 11/1973 | Anderson ............................ 73/23.41 |
| 3,926,561 | 12/1975 | Lucero .................................... 422/83 |
| 5,014,541 | 5/1991 | Sides et al. . |
| 5,492,838 | 2/1996 | Pawliszyn ............................ 436/178 |

OTHER PUBLICATIONS

Article by Yang et al., entitled "Multiplex Gas Chromatography: A Practical Approach for Environmental Monitoring", published in *trends in analytical chemistry*, 1996, vol. 15, No. 7, pp. 273–278.

*Primary Examiner*—Daniel S. Larkin
*Attorney, Agent, or Firm*—Edward H. Berkowitz

[57] ABSTRACT

A method and apparatus is provided for increasing sensitivity for near-real-time detection of very low concentrations of diffusely distributed trace vapors in a carrier medium. Before admitting the trace vapor bearing carrier medium into a near-real-time GC/MS trace vapor detection system, the concentration of the trace vapor in the carrier medium, air in this instance, is increased by passing it through a membrane gas separator. The gas separator preferentially passes a portion of the trace vapor and rejects all but a very small portion of the carrier medium. The sample, highly concentrated in trace vapor with respect to the carrier medium after passing through the gas separator, is then compressed by a turbomolecular pump resulting in a substantial increase in density of the trace vapor at the exhaust port of the pump and a corresponding increase in detection sensitivity.

32 Claims, 9 Drawing Sheets

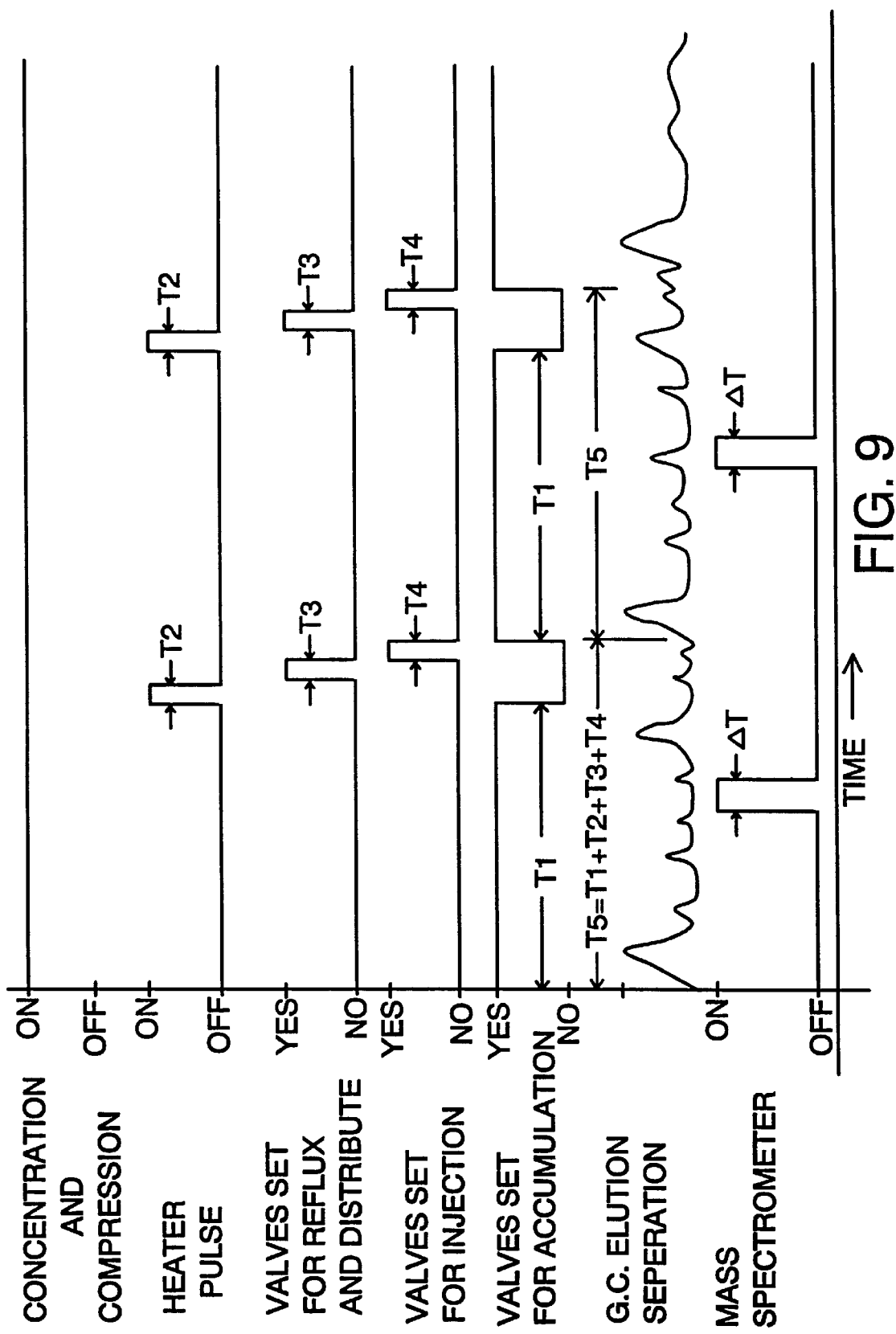

METHOD AND APPARATUS FOR SELECTIVELY EXTRACTING AND COMPRESSING TRACE SAMPLES FROM A CARRIER TO ENHANCE DETECTION

FIELD OF THE INVENTION

This invention relates generally to the detection of chemical species present in trace quantities in a carrier medium, and more particularly to the extraction and pre-compression of trace species in a sample to enhance their detection.

BACKGROUND OF THE INVENTION

The management of trace quantities of chemical species for the purpose of detection frequently involves the extraction of the targeted trace species as a vapor from a carrier medium in which it was originally dispersed. At very low trace density, for example, at concentrations below parts per million where the mode of detection responds to the targeted trace species and also to the accompanying carrier and other species that may be present, the competition of these accompanying materials for the detection events will frequently obscure the desired detection of the targeted trace species.

The terms "targeted trace vapors", "targeted material", and "targeted trace species" will be used interchangeably hereinafter to refer to a particular trace species of interest. Also, the terms "sampled medium" and "sampled mixture" will be used interchangeably hereinafter to refer to the mixture of the carrier medium and all trace species therein.

A common method used to avoid, in part, the vitiation of desired detection of the targeted material caused by the accompanying species in a mixture, is to pass a portion of the sampled mixture containing the targeted material through a separator inlet. A separator inlet is comprised of an aperture or surface which preferentially passes the targeted material at a higher rate while slowing, blocking, or diverting at least some of the other components of the sampled mixture, including in particular the predominant carrier.

A first representative example of such a separator inlet is an effusion separator (FIG. 1a), which includes a microporous cylinder or tube that may be made of sintered glass by way of example, and which is preferentially permeable to small molecules. This would be an appropriate separator if the sampled carrier medium consists exclusively of gases or vapors with the dominant constituent being small molecules of carrier gas. The larger molecules in the sampled medium, including the targeted material, are retained and pass through the entire length of the tube. Most of the smaller molecules are lost from the sample stream by effusion through the permeable walls of the tube and they are subsequently pumped away.

A second representative example of a separator inlet is a jet separator (FIG. 2). It relies on free expansion of a high velocity stream of the sampled medium injected through an inlet jet into a vacuum space. An exit skimmer is mounted coaxial with respect to the inlet jet and positioned close to it. The sampled medium passes through the inlet jet at near supersonic speed. Redistribution of momenta leaves the lighter molecules with more transverse velocity, and they are thereby less likely to enter the exit skimmer than the heavier molecules. The lighter molecules are thereby separated from the exiting sample gas stream and are pumped away.

A third representative example of a separator inlet is a membrane separator. FIG. 1b shows a single membrane separator and FIG. 3a shows a double membrane separator comprising two membranes in series. The membranes are largely impermeable to certain gasses, usually called permanent gasses, such as for example oxygen, nitrogen, and argon. A broad class of substances, hereinafter termed "the sample", that includes the targeted material, permeates the membranes more easily. For selected membranes, this class comprises substances having low polarity and high boiling point characteristic of organic materials. When molecules of the lower polarity, higher boiling point materials contact the inlet side of the membranes, they have a relatively high probability of sticking and being taken into solution in the membranes. Once in solution, they diffuse through the membranes at a rate proportional to the gradient of their concentration. They emerge at the outlet side of the membranes substantially separated from the carrier gas constituents. Most of the carrier that permeates the first membrane 26 is pumped away at the interstage, while more than one-half of the sample progresses to the second membrane 28. The output of the second membrane 28 can exit the overall separator 24 to a detector inlet at sub atmospheric pressure as shown in FIG. 3a or to an interior gas circuit 37 as shown in FIG. 3b. In either case, it is necessary to quickly remove the sample molecules from contact with the output side of the membrane in order to preserve the partial pressure gradient that drives their transport through the membrane.

Although utilizing a separator inlet enables an increase in the concentration ratio of the targeted material and is a form of pre-concentration in the sense that the ratio of the mass of the targeted material to the mass of the very small amount of carrier medium transmitted is increased, its utilization does not increase the density or partial pressure of the targeted material on a continuous basis at the separator output.

In earlier detection systems, pre-concentrating the sample, as heretofore described, generally improved sensitivity of the detection by reducing the ratio of permanent gasses to sample species introduced into the detector. However, the extent of improvement has been strongly dependent on the type of detector and the detailed manner in which the sample has been introduced and manipulated therein.

For successful detection in any practical system, not only must the quantity of the carrier gas be reduced, but also the quantity of targeted material in the sample must be above some minimum amount. In addition, the condition of the sample must be matched to the inlet requirement of the detection system within some tolerable range. The most relevant measure of the required condition of the sample is the density or partial pressure of the targeted material when introduced to the detection system. This measure can usually be translated to a specification of minimum detectability.

In a co-pending patent application incorporated herein below by reference, I describe another of my developments involving a near-real-time detection system using a gas chromatograph/mass spectrometer (GC/MS) tandem instrument to detect targeted materials dispersed in ambient air. To satisfy the input requirements of this advantageous detection method and to provide the desired detection at very low target ambient concentrations, substantial pre-concentration is needed first of all to match the impulse injection requirements of the GC and further to provide a sufficient mass flow rate of the targeted species for the MS to detect. In samples collected from the ambient, at very low trace detection levels for the targeted species, there will generally be higher concentrations of other trace component species, whose presence may obscure the desired detection in the MS. The function of the GC in the tandem GC/MS instrument is to provide a serial elution of the various species in the sample injected into the column after the separator has extracted the family of many trace constituents in the sampled medium from the carrier medium. The MS can then examine the targeted species in a unique time window with minimum interference from interfering species. The GC requires a very short pulse injection of the acquired sample in a minimum quantity of carrier gas, thus imposing a severe burden of pre-concentration on the management of the sample.

The older more traditional GC/MS technique, illustrated in FIG. 4, has been the analytical chemist's method of choice for analyzing certain types of chemical mixtures in the laboratory. In a traditional GC/MS system, the GC column separates sample components in their respective time of elution, and the components are individually sequentially analyzed by the mass spectrometer to provide definitive identification. Despite the exceptional capability of the traditional GC/MS system for analyzing trace levels in mixtures in the laboratory, its application to near-real-time detection of targeted materials dispersed in an ambient carrier has severe limitations. First, traditional GC has been generally characterized by elution times of many minutes and even hours to elute the components of mixtures into separate time windows, thereby defeating near-real-time performance. Second, to carry out the needed separation of the components of the mixture, the entire sample to be analyzed must be introduced into the GC in an impulse time that is less than the differences in elution times of distinguishable components. Third, the GC inlet is traditionally a closed port that excludes air. The sample is typically transported from the output side of the membrane to the GC by a carrier gas that contains no oxygen because, for many GC columns, the stationary phase can be degraded by oxygen, particularly at higher temperatures.

The limitations of the traditional GC/MS mentioned above, especially the low concentration of the targeted material in the ambient, work directly against the requirements of a system for making the near-real-time trace vapor detection. More recent GC/MS implementation employs capillary small-bore columns that are capable of short elution separation times. However, this exacerbates the requirement for the very short injection time required for GC operation. For ultra low concentration ratios, if just a very small increment of sample bearing carrier is injected in accord with the requirement for short impulse injection, the total amount of the targeted material will be below the minimum discernable limits of sensitivity of the MS detector. By way of example, gas or vapor injections into a nominal capillary GC column, scaled for the fast elution times required, must be less than about $10^{-5}$ liter in volume. Trace vapor samples, for example of molecular weight three-hundred, sought to be detected at 0.1 part per billion, will be present in the ambient at levels of about $1.36 \times 10^{-9}$ grams per liter. This would allow an injection of only $1.36 \times 10^{-14}$ grams, which is below the practical detection limit of the MS.

This example clearly illustrates the severe mismatch of the trace vapor sample condition and the inlet requirement of a near-real-time GC/MS trace vapor detector. My recent work, incorporated herein by reference, which is the subject of a co-pending patent application, Ser. No. 08/738,961, entitled "Real Time Trace Vapor Detection" of which I am the sole inventor, and which is assigned to the same assignee as the present invention, relates to a capillary GC/MS system which has been modified to adapt it for near-real-time detection of trace vapors in ambient air.

The aforementioned modifications disclosed in said co-pending application are comprised of; 1) providing an inlet membrane separator to concentrate a sample mixture of trace substances from the ambient air and to deliver the concentrated sample mixture to a suitable interior carrier gas stream; 2) providing a miniature vapor collection cold trap operating as a "micro accumulator" to capture the mixture of trace substances; and 3) providing a short thermal pulse to the cold trap, resulting in the impulse injection of the trace substances into the GC/MS system, wherein a fast GC/MS analysis is enabled.

Whereas the modified system heretofore described makes real-time GC/MS trace vapor detection and analysis possible, the system sensitivity is not sufficient for fast near-real-time response when dealing with ultra low concentration trace vapors dispersed in air. Greater density of the trace vapor samples in the carrier medium in short periods of time is required to enable greater sensitivity.

SUMMARY OF THE PRESENT INVENTION

An object of this invention is to improve the sensitivity of systems used for the detection of trace chemical species in a carrier medium.

Another object of this invention is to provide a method for increasing the concentration and for compressing trace vapor samples in a carrier medium.

Another object of this invention is to provide apparatus for increasing the concentration and for compressing trace vapor samples in a carrier medium.

Another object of this invention is to provide a method for improving the detection sensitivity for very low concentrations of trace vapors in atmospheric air samples.

Another object of this invention is to provide apparatus for improving the detection sensitivity for very low concentrations of trace vapors in atmospheric air samples.

Another object of this invention is to provide a method to increase the mass of trace sample that can be presented in successive introductions as the pulses required for a near-real-time GC/MS trace vapor detection system.

Another object of this invention is to provide apparatus for increasing the mass of trace sample that can be presented in successive introductions as the pulses required for a near-real-time GC/MS trace vapor detection system.

BRIEF DESCRIPTION OF THE DRAWINGS

FIG. 9 is a time line sequence for real time operation of the preferred embodiment of the invention.

DETAILED DESCRIPTION OF THE INVENTION

In connection with FIGS. 1a, 1b, 2, 3a, and 3b, showing prior art, sample substances are partially separated from the carrier (for example, ambient air,) with outlet to the detection instrument comprising a mixture enriched in the ratio of the samples to the carrier gases transmitted. Although this affords some benefit, there is no increase in sample density (or partial pressure) of sample presented to the detecting instrument.

The objects of my invention are met by providing a separator method and a compressor means, the former to exclude a major proportion of the ambient carrier gas, and the latter to increase significantly the density or partial pressure of the samples transmitted by the separator.

In my preferred embodiment, as a first step, the ambient carrier which bears a trace of sample materials is presented to a membrane separator which passes carrier gas at a very low rate, while it passes sample materials at a much higher rate. The output of the separator is presented to a gas compressor which is able to ingest the small amount of carrier gas transmitted and is able as well, to reduce the pressure of the trace sample materials at its inlet. The compressor thereby maintains a partial pressure gradient across the membrane that promotes efficient transfer of the sample materials through the separator. The compressor then compresses the transmitted mixture, thereby increasing the density of the trace samples.

Using this method, it is possible to provide a continuous stream in which the ratio of sample to carrier is greatly increased, and in which the partial pressure of the targeted species is also increased in accordance with the capability of the compressor used. For one useful application of the method, with a fast (near-real-time) gas chromatograph (GC), coupled to a mass spectrometer (MS), the output of the compressor may be extracted and managed so as to be presented in a short pulse as required by the GC, but with increased sample density, thereby significantly increasing the capability of the already powerful GC/MS detection instrument to achieve ultra sensitive detection.

Figure 1A:
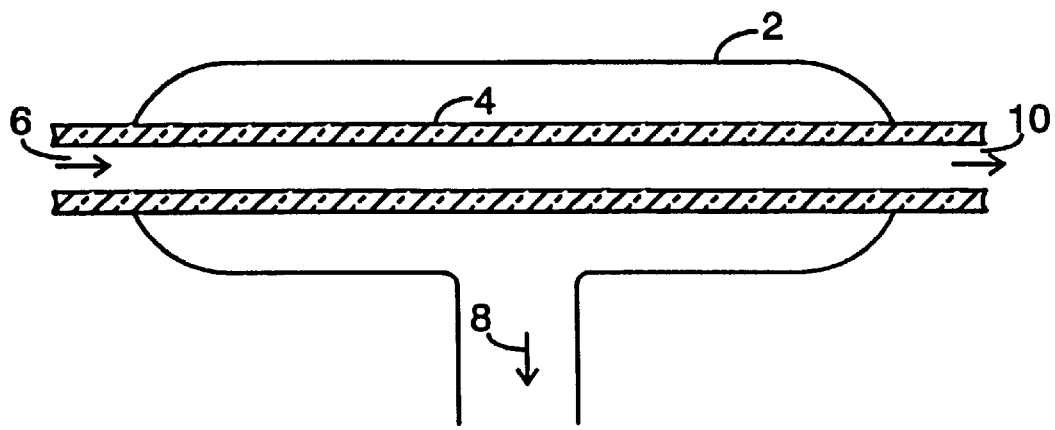
FIG. 1a shows a prior art effusion gas separator.

With reference to FIG. 1a, a prior art cylindrical or tubular gas separator 2 is shown. It is made of a microporous material 4 that is preferentially permeable to small molecules as heretofore described. The predominant constituents of the sampled mixture at the inlet 6 are small molecules, usually of the carrier medium. They effuse in large numbers out of the tube 4 into the surrounding region and are pumped away as shown by the arrow 8. Tubes of sintered glass and micro porous tetrafluoroethylene ("Teflon") have been used. The gas mixture sample at the outlet 10 is thereby enriched in the heavier molecules that include the targeted material. While this method affords some enrichment of the sample stream, the efficiency of the desired extraction of the lighter molecules is limited. To maintain a desired small enclosed volume, the tubing must be narrow in bore, thereby limiting the rate at which the desired larger molecules can be transmitted and preventing large gains in enrichment. Moreover, there will necessarily be a considerable reduction in the density or partial pressure of the desired components transmitted to a detecting device.

Figure 1B:
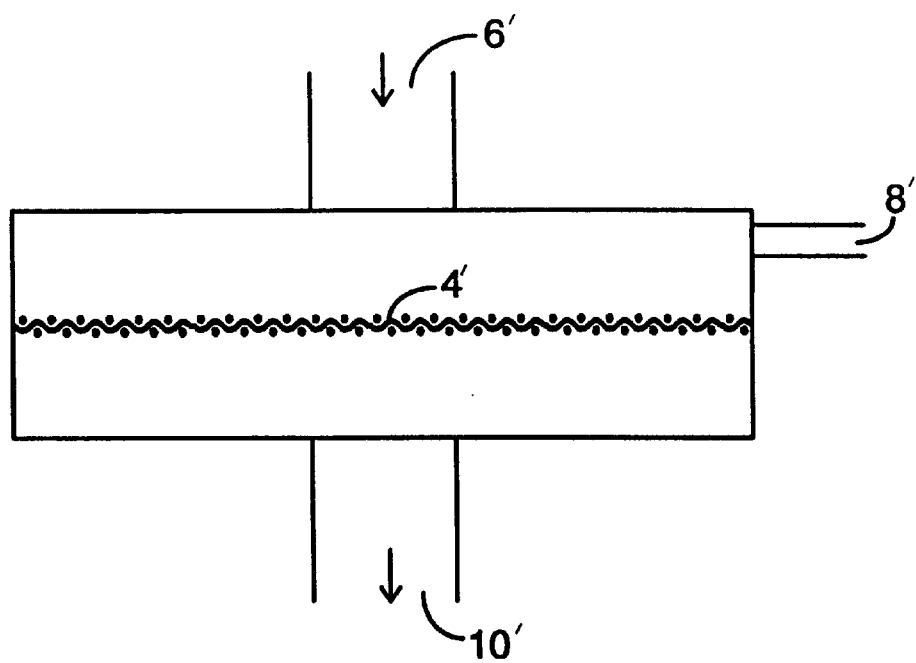
FIG. 1b shows schematically a prior art single stage membrane separator.

FIG. 1b schematically illustrates a single stage membrane separator having an input 6'. An exit 8' is furnished to release the carrier gas entering at 6' from which the sample has largely been extracted by the membrane 4'. The output 10' carries away the transmitted species, including a small quantity of the carrier gas and a proportionately larger fraction of the trace sample materials. This removal maintains the partial pressure gradient of the sample necessary to drive its transport through the membrane. With proper operation, an enrichment factor of one thousand in the ratio of sample to carrier can be achieved.

Figure 2:
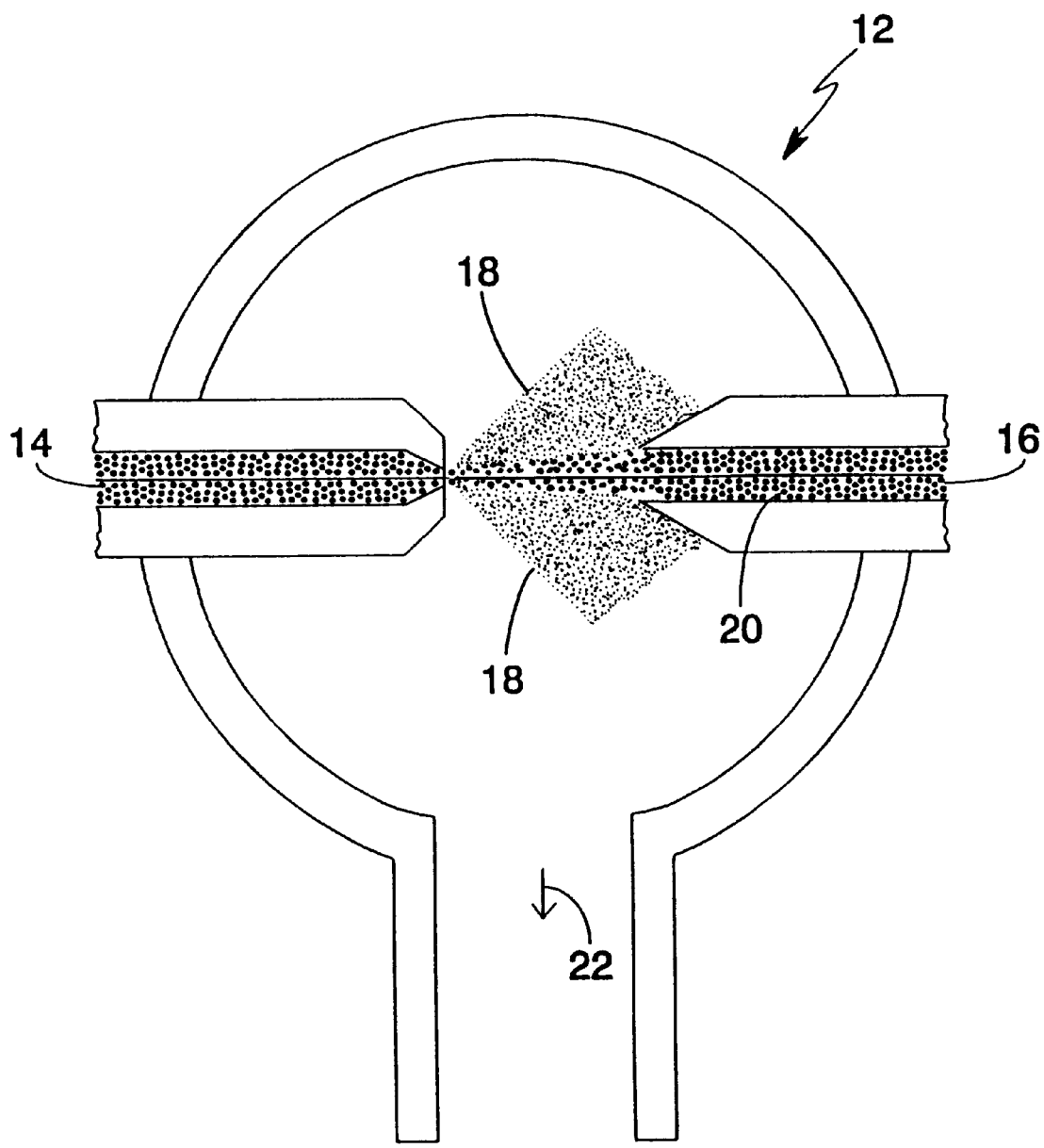
FIG. 2 shows a prior art jet gas separator.

With reference to FIG. 2, a prior art jet gas separator 12 is shown. As heretofore described, redistribution of momenta at the free expansion nozzle, and in some cases favorable diffusion rate differences, provide for enrichment of the sample gas mixture that passes from the input port 14 through the exit skimmer 16. The lighter molecules 18 are lost to the exiting gas stream 20 and are pumped away through pumping outlet 22.

Figure 3A:
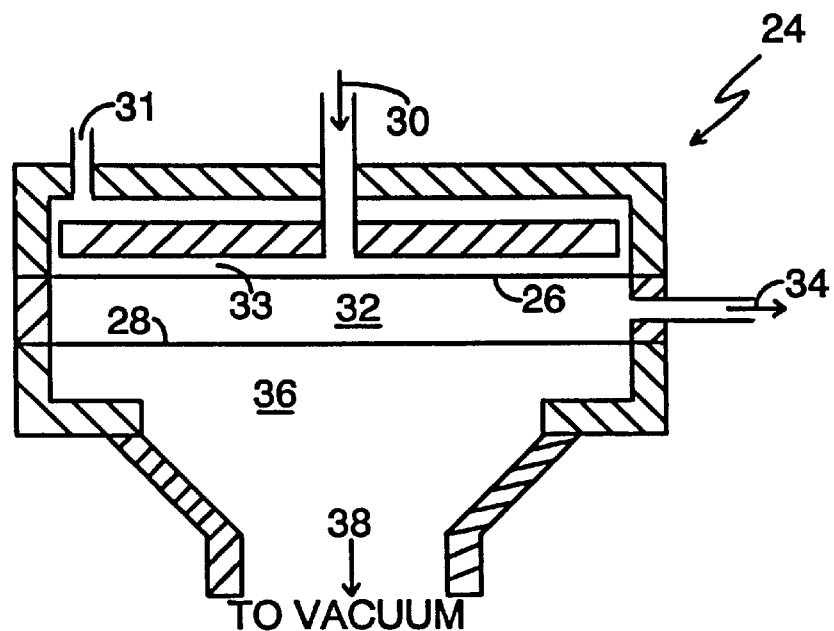
FIG. 3a shows a prior art two stage membrane type gas separator.

With reference to FIG. 3a, a prior art two stage membrane gas separator 24 comprised of two, dimethyl siloxane (silicone rubber) membranes 26, 28 is shown. The membranes 26, 28 typically have identical characteristics. Silicone rubber membranes exhibit different permeability for different materials. Molecules of materials having low polarity and high boiling point tend to permeate the membrane most readily as heretofore described. Substances like n-hexane, and most halogenated aliphatic compounds exhibit permeation rates one thousand times greater than the permeation rates of the permanent air gases. They even show a selectivity to exclude water vapor to some degree. In particular, the permeation through a single silicone membrane can be up to one thousand times greater for some gasses than it is for the air gases including oxygen and water vapor.

In the two stage separator of FIG. 3a, the sampled medium 30 is drawn into the inlet plenum 33 of the membrane separator by means of a sample inlet pump (not shown). Sample materials are extracted from the sampled medium 30 through the first membrane 26. The pump then removes the depleted carrier gas from the input plenum through input plenum exit port 31. The substances that have permeated the first membrane 26, including a very small amount of the carrier gas, are presented in the inter-stage space 32. An inter-stage vacuum pump (not shown), operated at a low pumping rate maintains an intermediate total pressure much lower than the exterior ambient pressure. The conductance of the inter-stage vacuum pumping port 34 is adjusted to be approximately equal to the conductance of the second membrane 28 for the sample substances. The exhaust through port 34 is non-selective, and since the conductance of the second membrane 28 is very low for the carrier gas, most of the carrier admitted to the inter-stage region is pumped away, and only a very small quantity passes the second membrane 28. With proper adjustment of pumping rates, the difference in permeation rates of the sample and carrier will provide an enrichment factor of up to one thousand for each stage and a combined enrichment factor that compounds this factor multiplicatively for the two membranes 26, 28. Enrichment factors as high as one million have been realized for two stage membrane separators.

To continue the transport of sample through the two stage membrane separator 24, the transported molecules must be removed from the output side of the second membrane 28 following their permeation through it. One method used is to pump them through exit port 38 out of the exit plenum 36, Because the total gas load is small, this can be accomplished by the inlet pumping of an instrument, such as a mass spectrometer. Alternatively, the transported materials can be carried away by the streaming of an interior carrier gas flow (usually of lower total volume than the total inlet stream) which will sweep the transported molecules away for detection. This latter configuration has come into use more recently, as it matches more nearly the inlet needs of the GC/MS system in a preferred embodiment of the present invention.

Figure 3B:
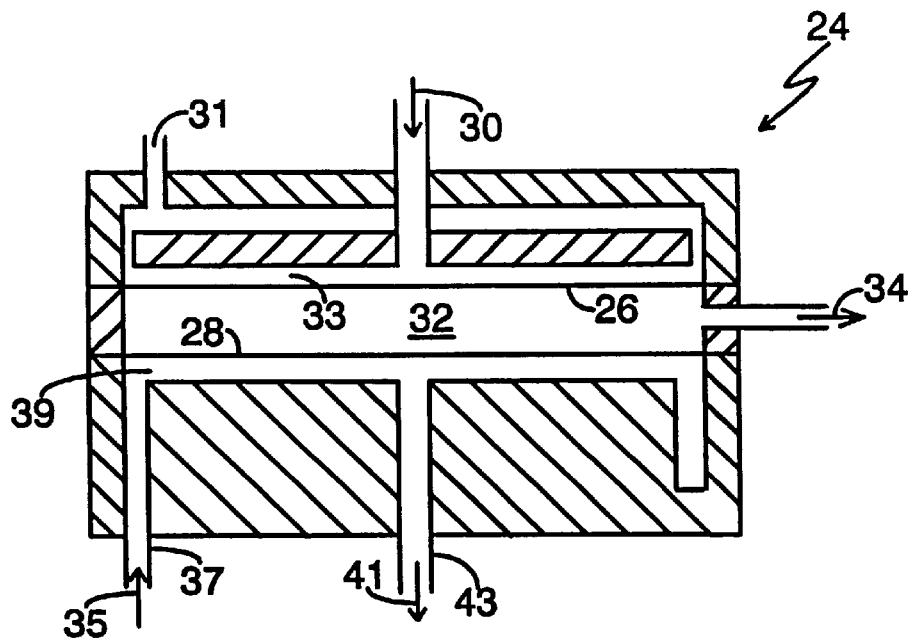
FIG. 3b shows the prior art two stage membrane type gas separator of FIG. 3a with the outlet side of the second membrane swept with an interior carrier gas.

With reference to FIG. 3b, the prior art two stage membrane separator differs from that shown in FIG. 3a only in the manner in which the molecules that permeate the second membrane 28 are swept away from its output side. In this embodiment, an interior carrier gas 35, chosen to match the inlet requirements of the detection system used, is introduced through a carrier gas input line 37. It sweeps across the output side of the second membrane 28 in the output plenum 39. The sample bearing interior carrier gas 41 exits the gas separator through the sample output line 43. If the detection system is a GC/MS, the preferred interior carrier gas, which also serves as the carrier gas for the GC may be helium.

Figure 4:
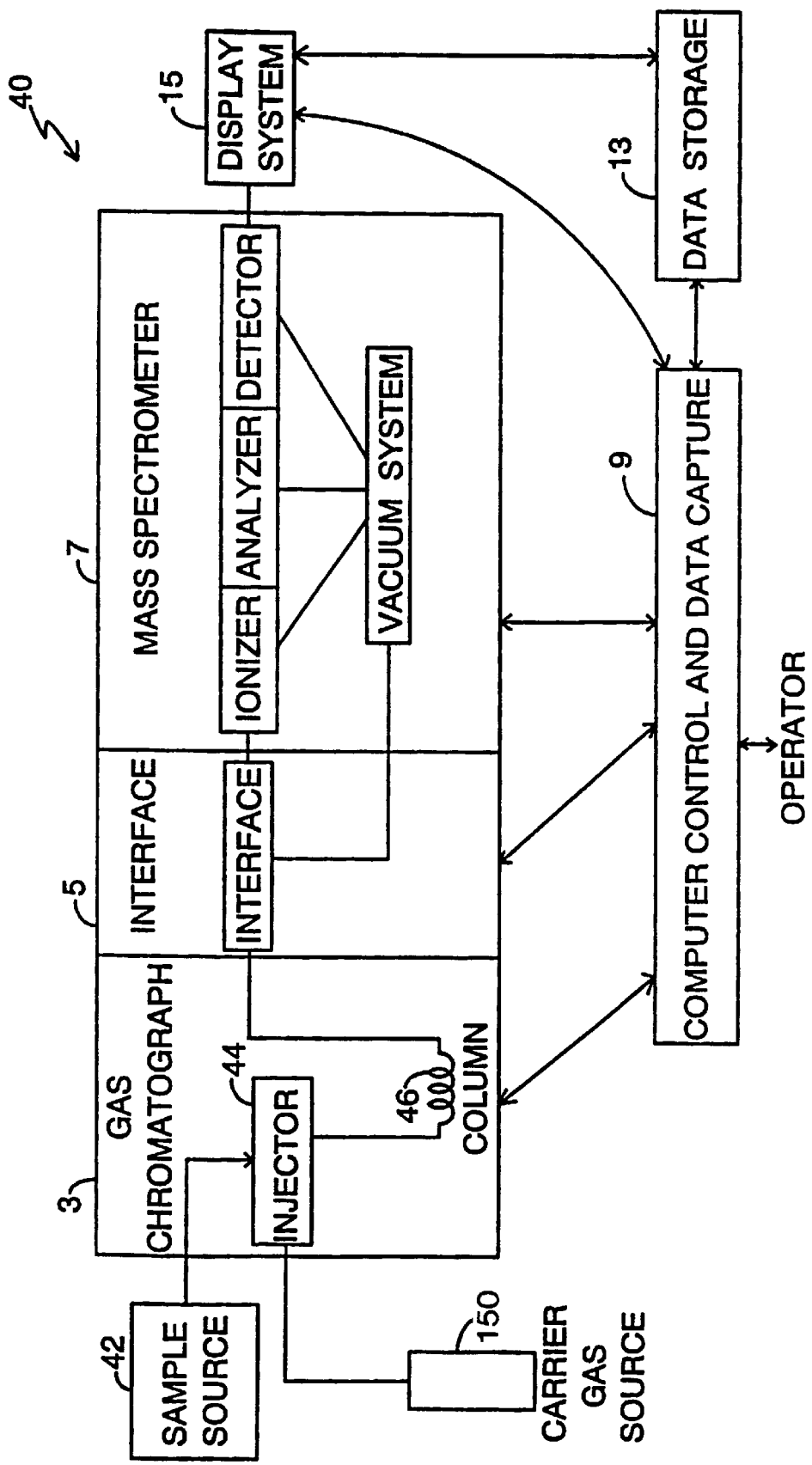
FIG. 4 is a block diagram of a prior art traditional laboratory GC/MS system.

FIG. 4 is a block diagram of a prior art traditional laboratory GC/MS system 40 used for detecting and analyzing chemical mixtures. Traditionally, specimens 42 to be analyzed are collected and brought to the system, with little, if any, concern for the time interval between collection and analysis. Correspondingly, there are many methods used for collection and preparation of the specimens 42 and many different injectors 44 and injection methods used to introduce the specimens 42 into the GC column 46 in a discreet concentrated impulse with the aid of carrier gas source 150. See, e.g., W. F. Coleman, *Trends in Gas Chromatographic Science*, 35 Journal of Chromatographic Science 350–351 (August 1997). The dual requirements of 1) near-real-time response and 2) sensitivity to low concentration of trace vapors highly dispersed in air, impose stringent requirements on the acquisition, preprocessing, and injection of the specimens into the GC/MS system. Similarly there are many types of interfaces 5 and mass analyzers 7. In recent years, these systems are under the control of a computer 9, which also provides control to a display 15 and data storage 13.

Figure 5:
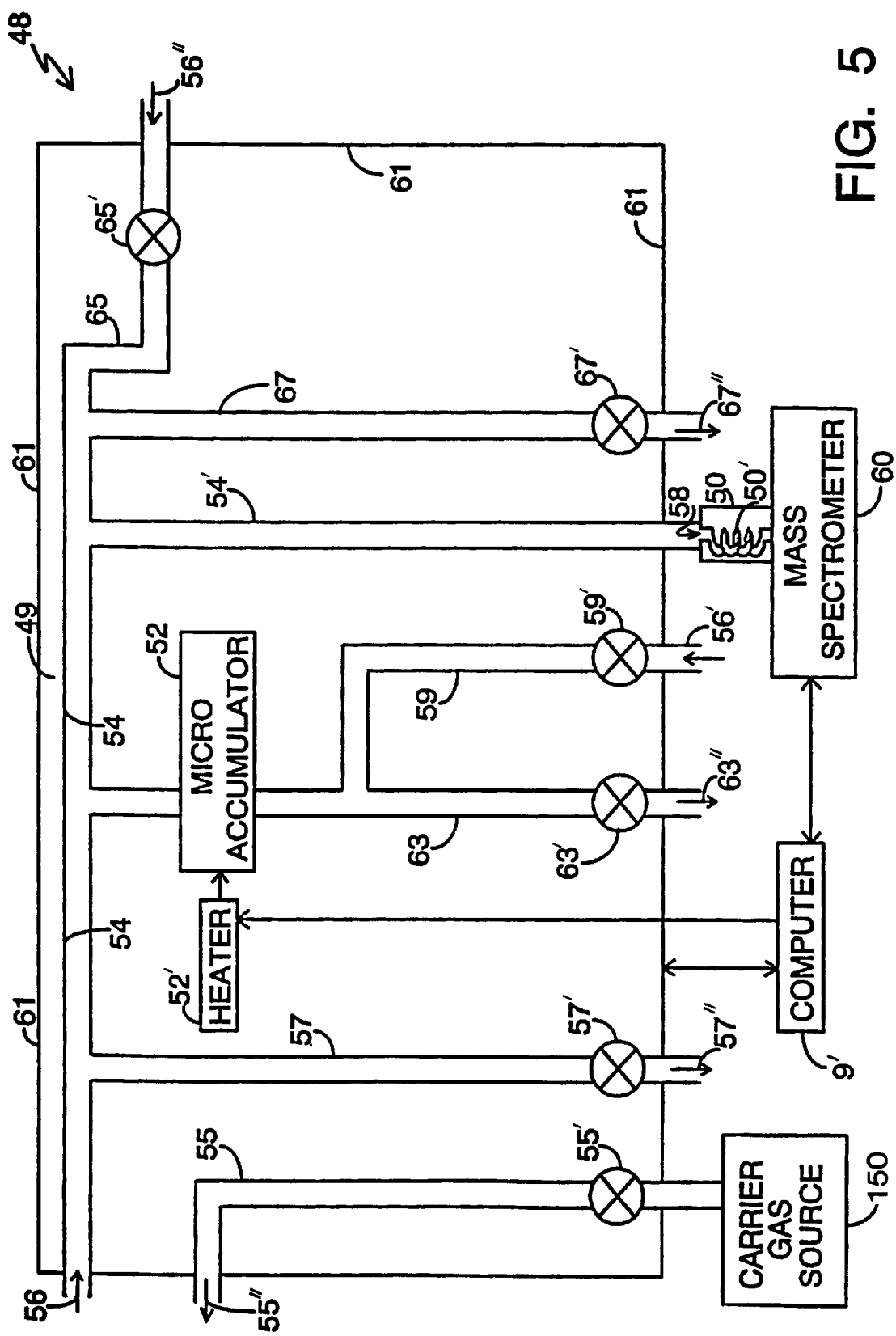
FIG. 5 is a schematic representation of a GC/MS system adapted for near-real-time trace vapor analysis.

FIG. 5 is a schematic representation of the previously referenced modified GC/MS system 48 adapted for near-real-time trace vapor analysis, the details of which have been incorporated herein by reference in connection with the above referenced co-pending patent application. This system utilizes an oven 50 that provides a temperature-controlled environment for a fast capillary GC column 51 that furnishes the short elution time required for near-real-time response in analysis. An auxiliary housing 61, which can be a separately heated oven, contains sample conduits, valves and other elements making up the inlet system portion 49 of the modified GC/MS system 48. The inlet system portion 49 also incorporates a sample trap 52 which may rely on chilling to extract and capture the trace sample components from the carrier gas stream presented to it, thereby serving as a micro accumulator for said trace sample components. When required, the accumulated trace sample components are released for reflux in a compact pulse, satisfying the inlet requirement of the GC column 50' for a very short injection time. The samples are typically released from the micro accumulator 52 by thermal desorption resulting from application of a fast thermal pulse applied to the micro accumulator by the heater 52'. The gas flow distribution tubulation portions 54, 54', 55, 57, 59, 63, 65, 67, and valve portions 55', 57', 59', 63', 65', 67', of the system provide for on-demand delivery of the sample-bearing carrier gas from the input port 56, to the previously mentioned micro accumulator 52, and subsequently to the inlet 58 of the GC column 50'. The sample bearing carrier gas may be derived from a clean carrier gas, supplied by an interior carrier gas source 150, sweeping sample components from the output of a membrane separator as described below and shown again in the preferred embodiment of FIG. 8. The mixed trace vapor sample then passes through the GC column 50', being separated thereby for presentation to the MS 60 for detection and analysis. The modified GC/MS system 48, excluding the oven 50, the GC 50' and the MS 60 will hereinafter be referred to as the "inlet system portion 49 of the modified GC/MS system".

The aforementioned valves 55', 57', 59', 63', 65', 67', may be located outside the walls of the heated box 61. They are typically electrically activated, controlled by the computer to establish the flow rates, timing, and distribution of the gas flow in the circuit. The valves have low volume to minimize time delay in switching them on and off. Humphrey Products Company of Kalamazoo, Mich. furnishes a suitable commercially available valve. Humphrey model HV01E1 has been successfully used in this application.

Still referring to FIG. 5, there are three principle gas flow inlet ports, 56, 56', and 56" in the inlet system portion 49 of the modified GC/MS system 48. Sample bearing carrier gas, derived by way of example from clean carrier gas sweeping the outlet side of a membrane separator is delivered through the first of these ports 56. The flow rate of the sample bearing carrier gas is controlled by valve 55' that may be incorporated into the inlet system portion 49. The carrier gas passes through tubulation 55 and exits through port 55" to sweep the membrane separator before returning to the sample bearing carrier gas inlet port 56. A gas diversion line 57 with a control valve 57' and a diversion exit port 57" may be furnished as a means of quick clearing of manifold 54 if overload sample conditions occur. This valve, when opened, will prevent sample from moving forward in the tubular manifold 54 and beyond to the micro accumulator 52, or the GC column entry 58. This gas diversion line is maintained closed in normal use.

In normal operation during a sample accumulation step, the inlet flow of carrier gas at port 56 passes along tubular manifold 54 and flows from there through the micro accumulator 52. The sample is trapped in the micro accumulator 52. The sample depleted carrier gas flows through valve 63', which is open during accumulation, and then exits through port 63 ". After a suitable time has elapsed, a reflux step is initiated. During this step of the operating cycle, the accumulated sample is recovered as a very short pulse from the micro accumulator 52, usually by thermal desorption induced by a fast thermal pulse from the heater 52'. Prior to the thermal release of the sample, valves 55', 63', and 65' are closed, and simultaneously valve 59' is opened. This operation of valves under precise computer control results in an uninterrupted and constant flow of carrier gas delivered to the GC inlet 58. When the flow is established by these valve settings, the thermal pulse to the micro accumulator is supplied. The flow of distribution gas entering through port 56' picks up the sample that has been thermally released from the micro accumulator and conveys it via the manifold 54 and tubulation 54' to the GC inlet 58. Flow in this reversed direction through the micro accumulator requires only enough time for the delivery of the sample as a short pulse for injection into the inlet of the GC, whereupon valve 59' can be closed and valve 65' can be opened. This provides GC carrier gas, entering at port 56', for driving the sample through the GC and MS.

A second gas diversion line 67, valve 67', and port 67" may be furnished to serve the same function as was served by line 57, valve 57', and port 57". In normal operation valve 67' is closed. In the event of a severe sample overload, valve 67' may be opened to extract excess sample from the manifold 54 and exhaust it via port 67". This action will quickly bring about a recovery to normal operation from sample overload conditions.

The operation of the modified GC/MS system can accordingly be characterized as a continuous repetitive three phase cycle. In phase one (accumulation), the sample is accumulated on the cold trap/micro accumulator 52 from the sample bearing carrier gas. In phase two (reflux), the accumulated sample is freed from the accumulator 52 by a rapid thermal pulse from the heater 52' and transported to the input of the GC column 50' by the distribution carrier gas. In phase three (separation and detection), the sample is driven by the GC carrier gas through the GC column 50' for elution separation and then through the MS 60 for analysis. Phase three of the cycle and phase one of the successive cycle can be made concurrent.

Operation is under control of computer 9' as described in FIG. 4.

Figure 6:
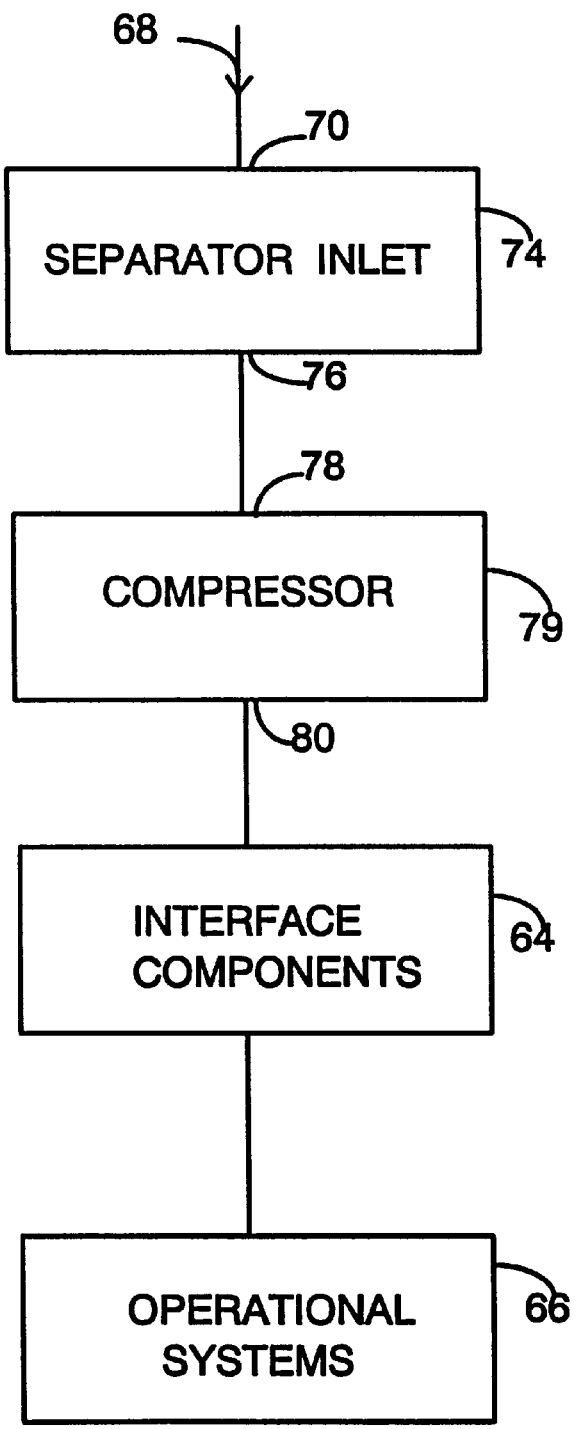
FIG. 6 is a functional block diagram of a system including the essential features of the present invention.
Figure 7:
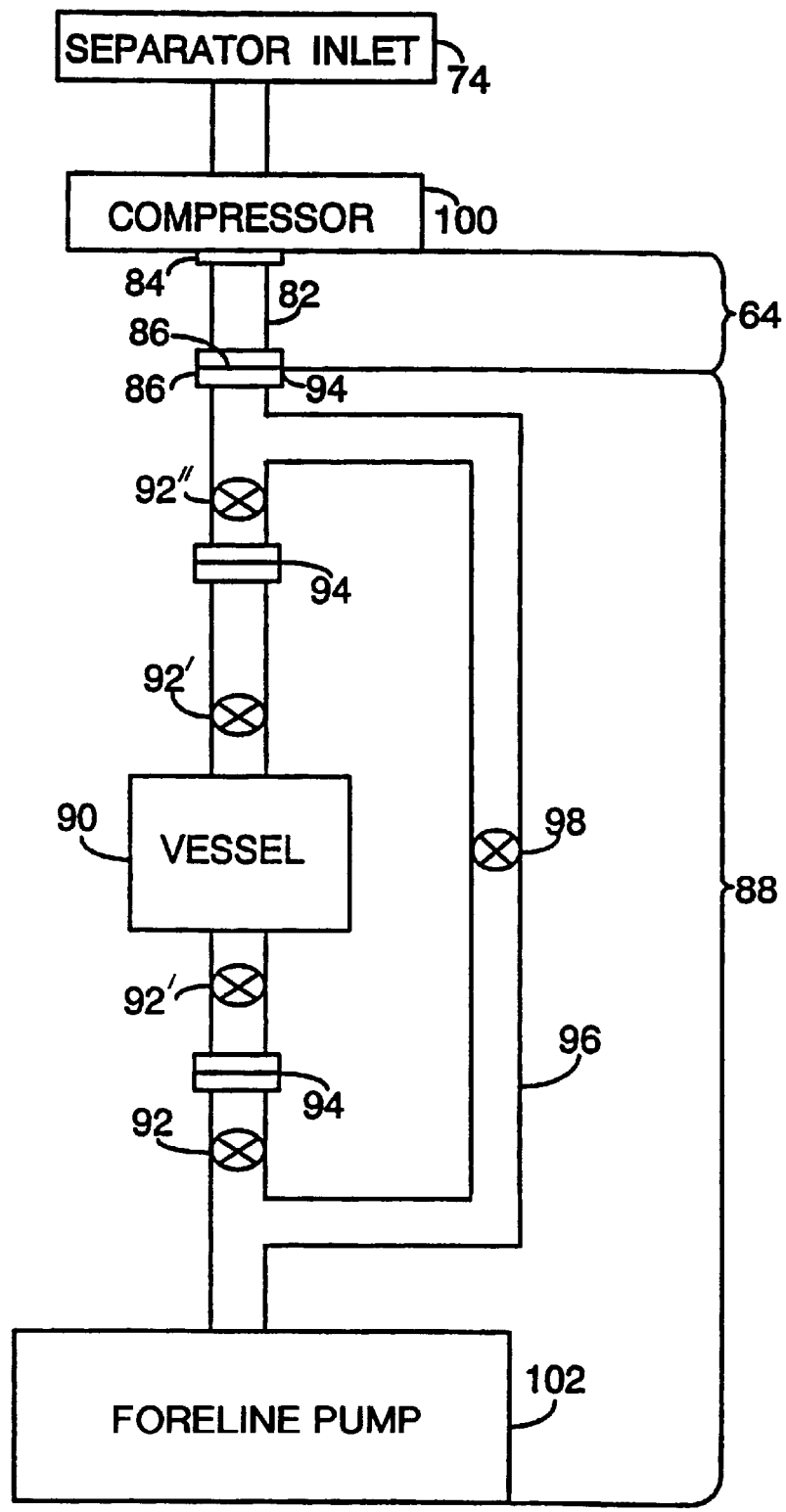
FIG. 7 is a schematic representation of a simple system embodiment utilizing the present invention.

FIG. 6 is a functional block diagram showing the essential system elements of the present invention and how they relate to one another. Still referring to FIG. 6, the sampled medium 68 including trace elements and a carrier gas communicates with the input side 70 of the separator inlet 74. A mixture of trace materials including a portion of the targeted material plus a very small amount of the carrier medium passes through the separator inlet 74 to its output side 76 which communicates directly with the input port 78 of the compressor 79. The sample is compressed and emerges at the compressor output/exhaust port 80. At this point, the targeted material as well as the other trace materials in the sample, in addition to being more concentrated in the carrier medium, also will have a substantially higher density/partial pressure than they had in the original sampled medium 68. The compressed sample passes from the compressor exhaust port 80 through one or more interface components 64 wherein it may be further modified as required to adapt it to the inlet requirements of an operational system 66. The operational system can be described most generally as any system that operates on the modified compressed sample to produce a desired result or effect.

Referring to FIG. 7, the interface components 64 described in FIG. 6 are shown schematically in a simple embodiment as an unobstructed passage 82 through which the compressor exhaust port 84 communicates directly with the inlet port 86 of an operational system 88. Still referring to FIG. 7, a simple embodiment of an operational system 88 could comprise a vessel 90 for accumulating, confining, and rendering available for subsequent transport, portions of the concentrated and compressed sample. Valves 92, 92' 92" and connectors 94 used in conjunction with bypass line 96 and bypass valve 98 are shown to indicate how the aforementioned vessel 90 could be connected to and disconnected from the system 88. This system could operate at sub atmospheric pressure using a vacuum pump such as a turbomolecular pump as compressor 100 used in conjunction with a foreline pump 102, or alternatively could be pressurized using a compressor such as a turbine 100 used in conjunction with a pressure vessel 102. The type of separator inlet 74 chosen would be appropriate for the operating pressure range of the system. Vent valves for safety and for enabling easy installation and removal of vessel 90 are assumed but not shown.

Still referring to FIG. 7, when vessel 90 is not installed or is being installed or removed from the system 88, valves 92 and 92" are closed and valve 98 is open. In this condition, compressor exhaust port 84 communicates directly with foreline pump 102 or pressure vessel 102 through the bypass line 96. Vessel 90 attaches to system 88 at connectors 94. If necessary, vessel 90 can be evacuated or pressurized prior to use by opening valves 92 and 92' and closing valves 92" and 98. To collect a sample in vessel 90, valves 92, 92', 92" are opened and valve 98 is closed. After collecting a sample, valves 92' are closed to retain the sample in the vessel 90. Then, the system is vented, valves 92 and 92" are closed and valve 98 is opened to enable removal of the vessel.

FIG. 8 is a schematic representation of a preferred embodiment of the invention. In this embodiment, the separator inlet prior to the compressor 106 is shown as a single stage membrane separator 104 positioned across the inlet 108 to a turbomolecular pump 106. The compressor in this embodiment comprises a turbomolecular pump 106. For a given throughput and compression ratio, the size of the separator inlet 104, i.e. the area of the membrane, is chosen such that the amount of targeted material that permeates the membrane in a time T1 corresponding to the aforementioned accumulation phase, when present in the ambient at its lowest required detectability concentration, equals or exceeds the amount of targeted material required to meet the minimum detectability threshold of the detection instrument. By way of example assume the following parameter values for near-real-time operation.

Targeted species in ambient air: tri-nitro toluene (TNT), molecular weight=227

Required detectability of targeted species at concentration of: $1{:}10^{11}$ in air.

Accumulation time ($T_1$): 10 seconds

Concentration of minimum targeted species after membrane separator: $1{:}10^{8}$ Throughput of turbomolecular pump: $10^{-2}$ Torr-liter per second Compression ratio of turbomolecular pump greater than: $10^{5}$ Minimum target species sample size per cycle required for detectability. $10^{-11}$ grams The minimum membrane area required, to acquire the necessary target species sample size per measurement cycle using these parameters will be approximately 100 $cm^2$ as shown in the following calculation.

The permeation rate R is found from the permeation equation $$R=P\times A\times \text{gradient } p \quad (1)$$

where R is the permeation rate in units of "atmosphere cc per second", P is the permeability (a materials constant with slight dependence on temperature), A is the area of the membrane in centimeters squared, and gradient p is the gradient of partial pressure in the membrane. For this calculatlion, it is usual to express gradient p in units of "partial pressure difference in centimeters of mercury per centimeter of membrane thickness". In these units, P has a value for the permanent air gases, and a value about one thousand times greater, i.e. approximately $3\times10^{-5}$ for the condensable target materials.

One atmosphere cc of 100% TNT vapor has a mass of $10^{-2}$ gram. At a dilution to $1{:}10^{-11}$, there will be a mass of $10^{-13}$ grams of TNT per cc of carrier gas at the required detectability threshold. Since the mass of TNT that is required per cycle for detection in this example is $10^{-11}$ grams, all of the targeted TNT vapor contained in 100 cc of carrier must be delivered to the detector. For a ten second cycle time, the required rate R of sample extraction at the separator will be $10^{-2}$ grams per second, or $10^{-2}$ atmosphere cc per second. With this requirement, equation (1) may be rewritten as follows:

$$A = R/(P_{TNT}) \times (\text{gradient } p) \qquad (2)$$

($P_{TNT}$) is approximately $3 \times 10^{-5}$. Assuming a membrane thickness of 0.0025 cm and an ambient partial pressure of $10^{-11}$ atmosphere=$7.6 \times 10^{-10}$ centimeters of mercury, gradient p=$3.04 \times 10^{-7}$. With these values, assuming a completely lossless system, the membrane area A required would be 11 cm$^2$. Prudence requires allowance for losses. Therefore, a membrane area in the range of fifty to one hundred square centimeters would be appropriate in this example.

Figure 8:
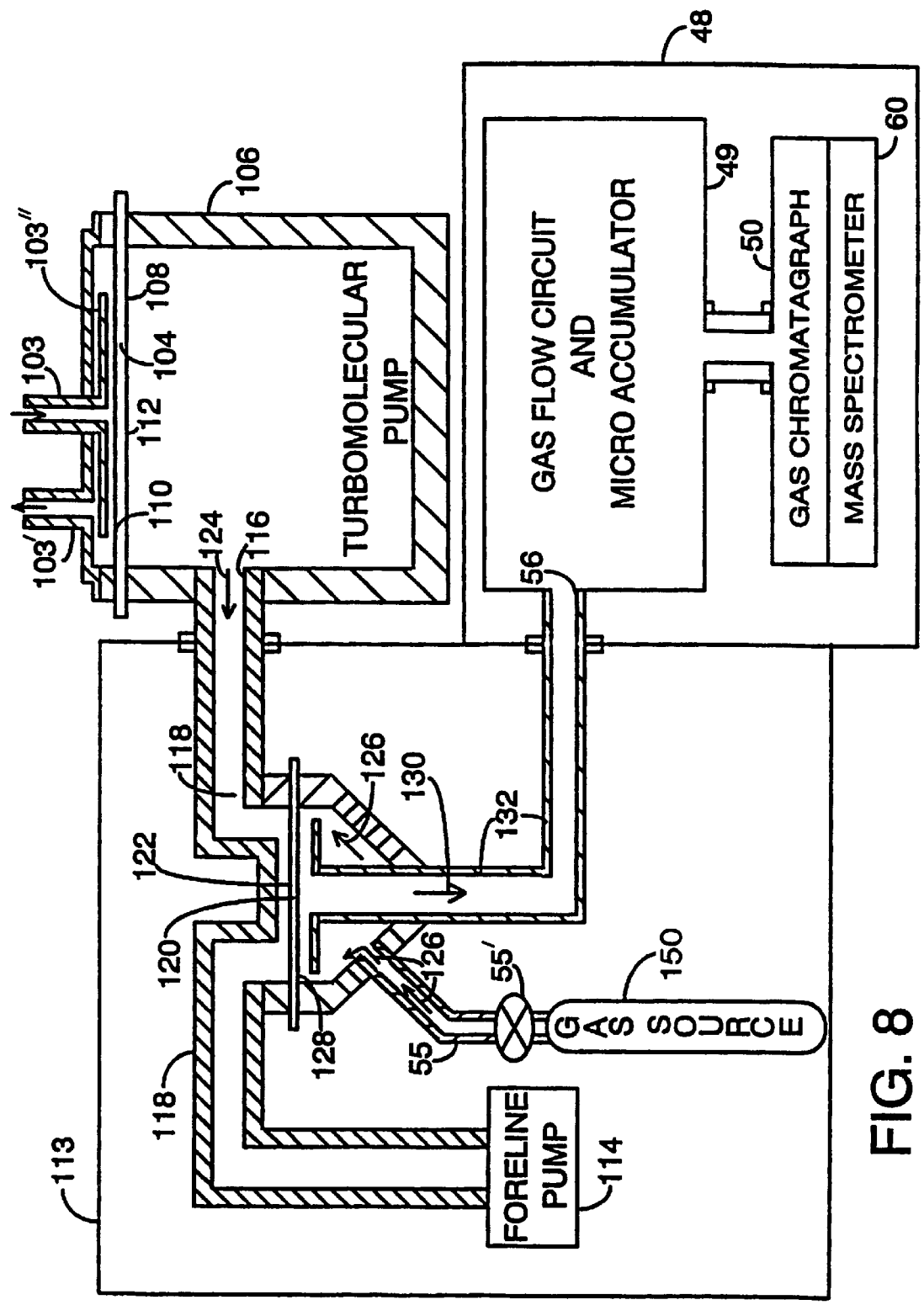
FIG. 8 is a schematic representation of a preferred embodiment of the invention.

Still referring to FIG. 8, the sampled medium 103 is drawn into the membrane gas separator by an input pump (not shown), pumping on the input pump line 103'. It is continuously distributed over the input side 110 of membrane 104 by a close spaced baffle plate 103" which assures a continuous adequate supply of target species to the input side 110 of the membrane 104. In operation, the partial pressures on the input face 110 and on the output face 112 of the membrane 104 will adjust to the overall throughput of the process. Permeation of the sample components through the membrane 104 is efficient because the reduced pressure provided by the turbomolecular pump 106 at the output side 112 of the membrane 104 ensures that a good partial pressure gradient is maintained to drive their transport.

Sample utilization is unusually good in this configuration. In contrast to other separators in current use, as heretofore described, wherein in each case some of the sample taken in is sacrificed in the process of separation, in this configuration, substantially all of the sample that permeates the membrane is retained and delivered to the turbomolecular pump output 116. Despite the reduced absolute pressure at the turbomolecular pump input 108, the entire sample is delivered to its output in a highly compressed state relative to the separator inlet pressure because of the very high compression ratio of the turbomolecular pump. Compression ratios for nitrogen are typically in the range of $10^7$, and the ratio for more massive molecules is even higher. The actual compression ratios achieved will depend on the details of the gas load and the exhaust pumping used, but the high ratios that can be achieved are well suited to the application in this invention.

The interface components 113 in this preferred embodiment comprise a foreline pump 114 that is connected to the turbo exhaust port 116 by a foreline passage 118. The interface components are further comprised of second membrane separator 120, the input face 122 of said second membrane separator 120 communicating with the aforementioned foreline passage 118. This passage is of a size to slightly constrict the flow of the exhaust from the turbomolecular pump 106 to allow efficient extraction of sample by the second membrane separator 120. A usable portion of the highly compressed sample is extracted from the turbo exhaust gas stream 124 through the second membrane separator 120. An interior inert gas carrier stream 126 sweeps the extracted portion of the highly compressed sample away from the output face 128 of the second membrane separator 120 into tubulation 132. The interior gas carrier stream 126 can flow at an arbitrary rate and pressure through tubulation 55 under control of valve 55' as required by the detector system used. The double membrane separator 24 shown in FIG. 3b may be suitable as the second membrane separator in this application where greater concentration ratio is required to satisfy the specification for optimum performance.

For the preferred embodiment of FIG. 8, the final detector shown is a GC/MS with the micro accumulator sample management means described above in connection with FIG. 5. The sample bearing interior carrier gas stream 130, controlled by valve 55' is directed, by interface tubular components 132, to the sample-bearing carrier gas input port 56 of the inlet system portion 49 of the near-real-time trace vapor detection system 48, shown here and in greater detail in FIG. 5. The interface components are chosen to provide the sample-bearing carrier gas conditions required by the aforementioned inlet system portion 49 of the modified GC/MS system 48 as described in connection with FIG. 5.

With reference to FIG. 9, sequence information is provided for near-real-time operation of the preferred embodiment for detection and analysis of trace organic drug vapors in ambient air, in which T5, the total cycle time, is less than ten seconds. In order to accommodate the short cycle time specified, the time elements T making up the cycle must be kept correspondingly short. To retain the needed GC resolution, the injection impulse time growing out of T2, T3, and T4 should be less than one tenth the total cycle time T5. In typical applications, the targeted detection in the interval ΔT is usually sufficiently separated from many components in the total sample that can be much larger than the targeted species. Because the desired detection cycle is limited to times as small as ten seconds, the importance of acquisition of sample from large quantities of ambient air and sufficient separation and major compression of the sample are all of great importance. The method of the present invention furnishes a unique and feasible means to accomplish the required separation and compression. In the example shown, final detection is by the mass spectrometer with repeated scans during the interval ΔT covering the mass range suitable to the targeted species.

A feature of the invention described herein is the combination of a separator inlet in series with a compressor. This combination of components, operating on a trace sample bearing carrier medium introduced at the separator inlet, results in an increase in the concentration and partial pressure of the trace constituents in the carrier medium at the compressor exhaust port. Although the preferred embodiment described in the disclosure has just two membrane separators, separated by a turbomolecular pump, it is not intended that the invention be limited to that configuration. Rather it is intended that the invention be interpreted broadly as being applicable to the essential features as heretofore described, utilizing any type compressor in combination with any configuration of components for interfacing the compressor exhaust port with any operational system. Although in the disclosure, the invention was applied only to the detection and analysis of trace constituents in air, it should be understood that other applications of the invention with carrier media other than air and other embodiments incorporating the essential features of the invention may be made without departing from the spirit and scope of the invention. In accordance with these considerations, the scope of the invention should be construed in view of my claims. With this in mind,

What is claimed is:

1. An improved inlet system for increasing the concentration ratio and the density of trace vapors diffusely dispersed in a carrier medium forming an input mixture, which input mixture is, in operation, provided to an input of said inlet system and where said trace vapors in said input mixture are at a first concentration ratio with respect to said carrier medium and at a first density value in said input mixture, the improvement comprising:

a membrane apparatus having an input and an output, said membrane apparatus input for receiving said input mixture and for preferentially extracting a portion of said trace vapors from said carrier medium and for providing a second higher concentration ratio of said trace vapors with respect to said carrier medium at said membrane apparatus output than said first concentration ratio at said membrane apparatus input and;

a compressor having an input and an output, said compressor being a turbomolecular pump;

said membrane apparatus being fixedly disposed across said input of said turbomolecular pump whereby, in operation, said membrane apparatus provides at said output said second higher concentration ratio of trace vapors and said turbomolecular pump establishes and maintains a partial vacuum at said output of said membrane apparatus and thereby maintains a pressure driving gradient of said trace vapors across said membrane apparatus while simultaneously providing higher density of said trace vapors at said output of said turbomolecular pump compared to the density of said trace vapors at said input of said turbomolecular pump whereby the density of said trace vapors at said output of said turbomolecular pump is at a second density value which is higher than said first density value.

2. An apparatus for concentrating and compressing trace vapor constituents dispersed in a carrier medium comprising:

separator inlet for extracting a portion of said trace vapor constituents from said carrier medium in which said constituents are dispersed, said separator inlet having an input side and an output side wherein a first portion of said trace vapor constituents, after communicating with said input side, traverses said separator inlet to said output side, and wherein a second portion of said carrier medium, after communicating with said input side, traverses said separator inlet to said output side; and a compression means having an input port and an output port, said input port communicating directly with said output side of said separator inlet, said first portion of said trace vapor constituents and said second portion of said carrier medium being compressed by said compression means, said first portion of said trace vapor constituents having both a higher concentration with respect to said carrier medium and a higher density, at said output port of said compression means than said concentration with respect to said carrier medium and said density of said trace vapor constituents when diffusely dispersed in said carrier medium prior to traversing said separator inlet.

3. The apparatus of claim 2, wherein said separator inlet is a first membrane separator inlet comprised of at least one permeable membrane.

4. The apparatus of claim 3, wherein said compression means is a turbomolecular pump.

5. The apparatus of claim 4, further comprising an interface having at least one interface component and an operational system, said interface having an input end and an output end, said input end of said interface being connected to said output port of said turbomolecular pump, said output end of said interface being connected to a sample bearing gas input port of said operational system, said output port of said turbomolecular pump thereby communicating through said interface with said sample bearing gas input port of said operational system.

6. The apparatus of claim 5, wherein said operational system is a trace vapor detection system.

7. The apparatus of claim 6, wherein said trace vapor detection system is a near-real-time trace vapor detection system for detecting trace vapors dispersed in a carrier medium in a cycle time less than ten seconds.

8. The apparatus of claim 7, wherein said carrier medium is air.

9. The apparatus of claim 8, wherein said near-real-time trace vapor detection system is comprised of a serial connection of a gas chromatograph and a mass spectrometer.

10. The apparatus of claim 9, wherein said first portion of said trace vapor constituents are accumulated in an accumulator during the majority of time of operation of said trace vapor detection system and wherein said accumulated first portion of said trace vapor constituents are injected into said gas chromatograph during a minority time of operation of said trace vapor detection system.

11. The apparatus of claim 5, wherein said interface is comprised of a second membrane gas separator having at least one membrane, said second membrane gas separator being disposed between said output port of said turbomolecular pump and said sample bearing gas input port of said operational system.

12. The apparatus of claim 11, wherein said operational system is a trace vapor detection system.

13. The apparatus of claim 12, wherein said trace vapor detection system is a near-real-time trace vapor detection system for detecting trace vapors dispersed in a carrier medium in a cycle time less than ten seconds.

14. The apparatus of claim 13, wherein said carrier medium is air.

15. The apparatus of claim 14, wherein said near-real-time trace vapor detection system is comprised of a serial connection of a gas chromatograph and a mass spectrometer.

16. The apparatus of claim 15 wherein said first portion of said trace vapor constituents are accumulated in an accumulator during the majority of time of operation of said trace vapor detection system and wherein said accumulated first portion of said trace vapor constituents are injected into said gas chromatograph during a minority time of operation of said trace vapor detection system.

17. A method for concentrating and compressing trace vapor constituents dispersed in a carrier medium comprising the steps of:

extracting a portion of said trace vapor constituents from said carrier medium in which said trace vapor constituents are dispersed using a separator inlet, said separator inlet having an input side and an output side wherein a first portion of said trace vapor constituents after communicating with said input side, traverse said separator inlet to said output side and wherein a second portion of said carrier medium, after communicating with said input side, traverses said separator inlet to said output side; and inputting gas available at said output side of said separator inlet to a compression means having an input port and an output port, said input port of said compression means communicating directly with said output side of said separator inlet, said first portion of said trace vapor constituents and said second portion of said carrier medium being compressed by said compression means, said first portion of said trace vapor constituents having a higher concentration with respect to said carrier medium and a higher density, at said output port of said compression means than said concentration with respect to said carrier medium and said density of said trace vapor constituents when dispersed in said carrier medium prior to traversing said separator inlet.

18. The method of claim 17, wherein said separator inlet is a first membrane separator inlet comprised of at least one permeable membrane.

19. The method of claim 18, wherein said compression means is a turbomolecular pump which increases, in operation, the density of said first portion of said trace vapor constituents which exit said pump output port, said turbomolecular pump further maintaining a partial vacuum at said output side of said separator inlet and thereby maintaining a partial pressure driving gradient across said membrane of said separator inlet.

20. The method of claim 19, further comprising the steps of:

providing an interface having at least one interface component and an operational system, said interface having an input end and an output end, said input end of said interface being connected to said output port of said turbomolecular pump, said output end of said interface being connected to a sample bearing gas input port of said operational system; and flowing gas exiting from said output port of said turbomolecular pump through said interface to said sample bearing gas input port of said operational system.

21. The method of claim 20, wherein said operational system is a trace vapor detection system.

22. The method of claim 21, wherein said trace vapor detection system is a near-real-time trace vapor detection system for detecting trace vapors dispersed in a carrier medium.

23. The method of claim 22, wherein said carrier medium is air.

24. The method of claim 23, wherein said near-real-time trace vapor detection system is comprised of a serially connected gas chromatograph and a mass spectrometer, said gas chromatograph employing serial elution separation in a gas capillary.

25. The method of claim 24, wherein said first portion of said trace vapor constituents are accumulated in an accumulator during the majority of time of operation of said trace vapor detection system and wherein said accumulated first portion of said trace vapor constituents are injected into said gas chromatograph during a minority time of operation of said trace vapor detection system.

26. The method of claim 20, wherein said interface is comprised of a second membrane gas separator having at least one membrane, said second membrane gas separator being disposed between said output port of said turbomolecular pump and said sample bearing gas input port of said operational system.

27. The method of claim 26, wherein said operational system is a trace vapor detection system.

28. The method of claim 27, wherein said trace vapor detection system is a near-real-time trace vapor detection system for detecting trace vapors dispersed in a carrier medium.

29. The method of claim 28, wherein said carrier medium is air.

30. The method of claim 29, wherein said near-real-time trace vapor detection system is comprised of a serially connected gas chromatograph and a mass spectrometer, said gas chromatograph employing serial elution separation in a gas capillary.

31. The method of claim 30, wherein said first portion of said trace vapor constituents are accumulated in an accumulator during the majority of time of operation of said trace vapor detection system and wherein said accumulated first portion of said trace vapor constituents are injected into said gas chromatograph during a minority time of operation of said trace vapor detection system.

32. The method of claim 19, which further comprises:

(a) in an accumulator, accumulating for a first time period (T1) said first portion of said trace vapor constituents which exit said output port of said compressor;

(b) immediately after said first time period (T1), releasing said accumulated first portion of said trace vapor constituents available in a second time period (T2) for transfer to the input of a gas chromatograph;

(c) immediately after said second time period (T2), refluxing said accumulated first portion of said trace vapor constituents from said accumulator to the input of said gas chromatograph in a third time period (T3);

(d) immediately after said third time period (T3), injecting said first portion of said trace vapor constituents into said gas chromatograph in a fourth time period (T4);

(e) separating said first portion of said trace vapor constituents by elution chromatography in a time period less than the total cycle time (T5), where (T5)=(T1+T2+T3+T4);

(f) inputting said elution time separated constituents into a mass spectrometer and spectrographically performing mass analysis over a selected range of masses in a time period less than the total cycle time (T5); and (g) repeating steps (a) through (f) in sequence every time period (T5) during the entire near-real-time trace detection operation.

* * * * *